(12) United States Patent
Zribi et al.

(10) Patent No.: US 7,505,128 B2
(45) Date of Patent: Mar. 17, 2009

(54) COMPACT, HAND-HELD RAMAN SPECTROMETER MICROSYSTEM ON A CHIP

(75) Inventors: Anis Zribi, Rexford, NY (US); Stacey Joy Kennerly, Niskayuna, NY (US); Glenn Scott Claydon, Wynantskill, NY (US); Long Que, Rexford, NY (US); Ayan Banerjee, Bangalore (IN); Shankar Chandrasekaran, Tamil Nadu (IN); Shivappa Ningappa Goravar, Karnataka (IN); David Cecil Hays, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 179 days.

(21) Appl. No.: 11/400,948

(22) Filed: Apr. 10, 2006

(65) Prior Publication Data
US 2007/0236697 A1   Oct. 11, 2007

(51) Int. Cl.
G01J 3/44 (2006.01)
(52) U.S. Cl. .................... 356/301; 356/326
(58) Field of Classification Search .............. 356/301, 356/417, 326
See application file for complete search history.

(56) References Cited

U.S. PATENT DOCUMENTS

| | | | |
|---|---|---|---|
| 2005/0030533 A1* | 2/2005 | Treado | 356/326 |
| 2005/0248759 A1* | 11/2005 | Wang et al. | 356/301 |
| 2006/0164636 A1* | 7/2006 | Islam et al. | 356/301 |
| 2007/0127019 A1* | 6/2007 | Zribi et al. | 356/301 |

* cited by examiner

Primary Examiner—Kara E Geisel
(74) Attorney, Agent, or Firm—Richard A. DeCristofaro (57) ABSTRACT

An integrated spectrometer instrument, including an optical source formed on a chip, the optical source configured to generate an incident optical beam upon a sample to be measured. Collection optics formed on the chip are configured to receive a scattered optical beam from the sample, and filtering optics formed on the chip are configured to remove elastically scattered light from the scattered optical beam at a wavelength corresponding to the optical source. A tunable filter formed on the chip is configured to pass selected wavelengths of the scattered optical beam, and a photo detector device formed on the chip is configured to generate an output signal corresponding to the intensity of photons passed through the tunable filter.

25 Claims, 6 Drawing Sheets

COMPACT, HAND-HELD RAMAN SPECTROMETER MICROSYSTEM ON A CHIP

BACKGROUND OF THE INVENTION

The invention relates generally to spectroscopy systems and, more particularly, to a compact, hand-held Raman spectrometer instrument.

Spectroscopy generally refers to the process of measuring energy or intensity as a function of wavelength in a beam of light or radiation. More specifically, spectroscopy uses the absorption, emission, or scattering of electromagnetic radiation by atoms, molecules or ions to qualitatively and quantitatively study physical properties and processes of matter. Raman spectroscopy relies on the inelastic scattering of intense, monochromatic light, typically from a laser source operating in the visible, near infrared, or ultraviolet range. Photons of the monochromatic source excite molecules in the sample upon inelastic interaction, resulting in the energy of the laser photons being shifted up or down. The shift in energy yields information about the molecular vibration modes in the system/sample.

However, Raman scattering is a comparatively weak effect in comparison to Rayleigh (elastic) scattering in which energy is not exchanged. Depending on the particular molecular composition of a sample, only about one scattered photon in $10^6$ to about $10^8$ tends to be Raman shifted. Because Raman scattering is such a comparatively weak phenomenon, an instrument used to analyze the Raman signal should be able to substantially reject Rayleigh scattering, have a high signal to noise ratio, and have high immunity to ambient light. Otherwise, a Raman shift may not be measurable.

A challenge in implementing Raman spectroscopy is separating the weak inelastically scattered light from the intense Rayleigh-scattered laser light. Conventional Raman spectrometers typically use reflective or absorptive filters, as well as holographic diffraction gratings and multiple dispersion stages, in order to achieve a high degree of laser rejection. A photon-counting photomultiplier tube (PMT) or a charge coupled device (CCD) camera may be used to detect the Raman scattered light.

Concurrently, there is a growing need for miniaturization of instruments for biological, chemical and gas sensing in applications that vary from medical to pharmaceutical to industrial to security. This is creating a paradigm shift in experimentation and measurement, where the trend is to bring the instrument/lab to the sample rather than bringing the sample back to the lab for analysis. Traditionally, the transportation of samples back to a lab for analysis using benchtop instruments has tended to slow down investigations and leads to backlogs. Accordingly, it is now desirable to be able to perform spectroscopy with shorter response times using "in the field" analysis, and with little or no sample preparation. Moreover, a spectroscopy device in this regard would preferably be a portable and compact instrument, providing higher selectivity and multiphase analysis capability at a lower cost with respect to conventional systems.

BRIEF DESCRIPTION OF THE INVENTION

The above discussed and other drawbacks and deficiencies of the prior art may be overcome or alleviated by an embodiment of an integrated spectrometer device, including an optical source formed on a chip, the optical source configured to generate an incident optical beam upon a sample to be measured. Collection optics formed on the chip are configured to receive scattered photons from the sample, and filtering optics formed on the chip are configured to remove elastically scattered light from the scattered optical beam at a wavelength corresponding to the optical source. A tunable filter formed on the chip is configured to pass selected wavelengths of the scattered optical beam, and a photo detector device integrated onto the chip is configured to generate an output signal corresponding to the intensity of photons passed through the tunable filter.

In another embodiment, a portable, hand-held spectrometer instrument includes a body having operator controls and an output display, an optical signal output port through which an internally generated incident optical beam is directed, and an optical signal input port through which a sample-scattered optical beam is received. The incident optical beam generated by an optical source formed on a chip housed within the body. Collection optics are formed on said chip, the collection optics configured to receive said sample-scattered optical beam. Filtering optics are formed on the chip, the filtering optics configured to remove elastically scattered light from the sample-scattered optical beam at a wavelength corresponding to the optical source. A tunable filter is formed on the chip, the tunable filter configured to pass selected wavelengths of the sample-reflected optical beam. A photo detector device is formed on the chip, the photo detector device configured to generate an output signal corresponding to the intensity of photons passed through the tunable filter.

These and other advantages and features will be more readily understood from the following detailed description of preferred embodiments of the invention that is provided in connection with the accompanying drawings.

DETAILED DESCRIPTION OF THE INVENTION

Embodiments of the invention disclosed herein include a compact, hand-held spectrometer device characterized by a fully integrated microsystem on a chip. Other embodiments include a microelectromechanical system (MEMS) tunable spectrophotometer, which may be used for multiple spectroscopic applications such as Raman, infrared (IR) absorption, etc. The spectrometer can achieve high resolution within a broad spectral range, consumes low power, is compact and is immune to thermal and vibration induced noises. Thereby, the device provides rapid, quantitative identification of bio and chemical analytes in gas, liquid and solid phases. This spectrometer may thus be used in applications as diverse as: rapid narcotics and explosives identification, water quality monitoring, just in time drug identification, blood analyte measurement, etc.

As is described herein after, the microsystem includes a monochromatic excitation photon source, an optofluidics module for sample preparation (optional), an (optional) optical power management system to avoid sample burning, light collection optics, guiding optics, collimating and focusing optics, a tunable filter, a photodetector, acquisiton electronics, conditioning electronics, device controllers, pattern recognition algorithms and sample signature data bases. As a result of the integration of the spectroscopy components into a microsystem, the spectrometer is portable, light, miniature (e.g., the size of a remote control or smaller), autocalibrated, high-resolution (e.g., better than 5 cm$^{-1}$) and offers rapid, quantitative identification of bio and chemical analytes in gas, liquid and solid phases.

In contrast to (for example) existing Raman systems that are bigger and heavier, the compact device of the present disclosure yields high performance, quantitative analyses that are comparable with desktop systems. Conversely, existing portable Raman systems offer lower performance, are still heavy (and hence more difficult to handle during measurements with long integration times), and do not allow for quantitative analysis.

Figure 1:
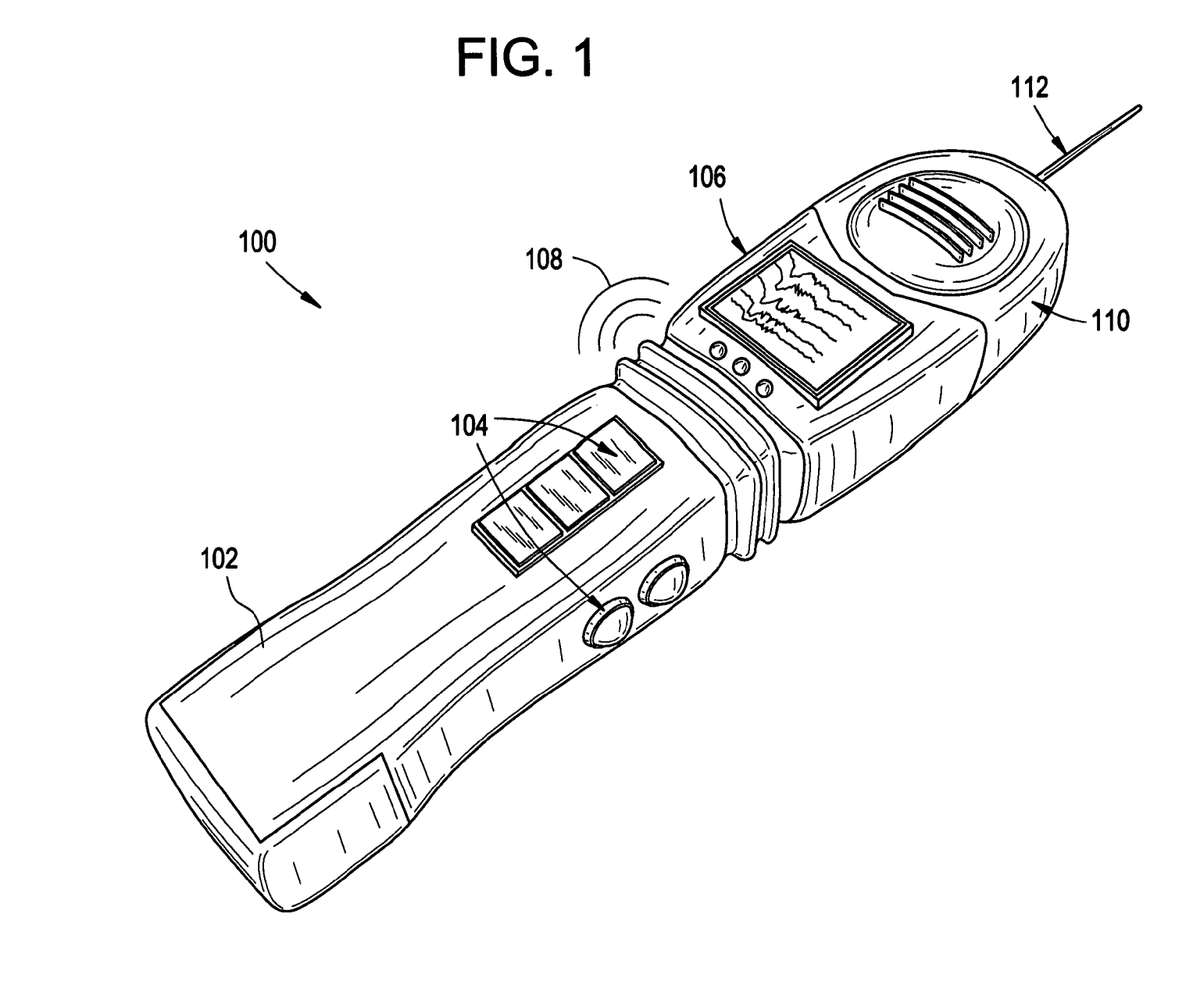
FIGS. 1 through 3 illustrate various perspective views of a portable Raman spectrometer device, in accordance with an embodiment of the invention.
Figure 2:
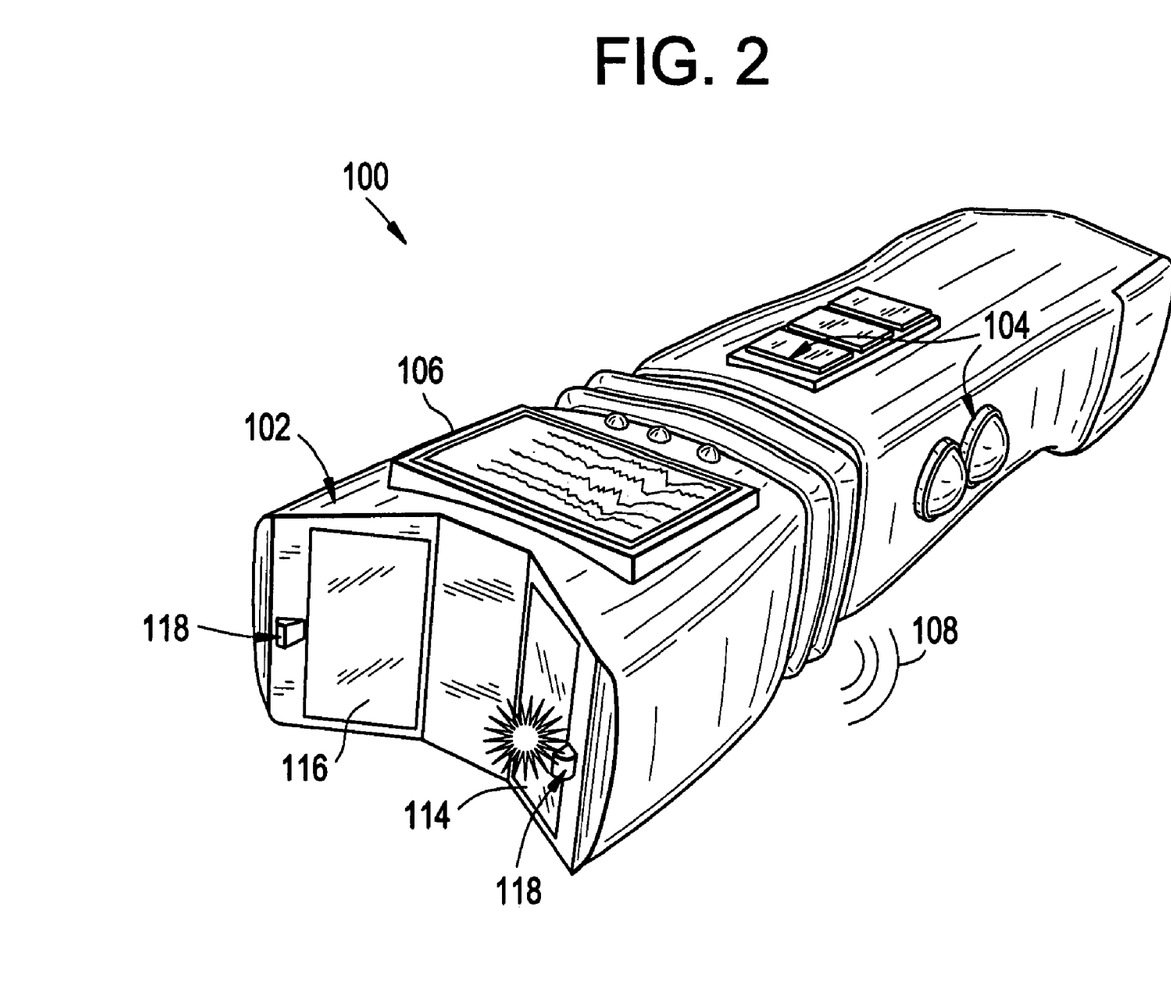
Figure 3:
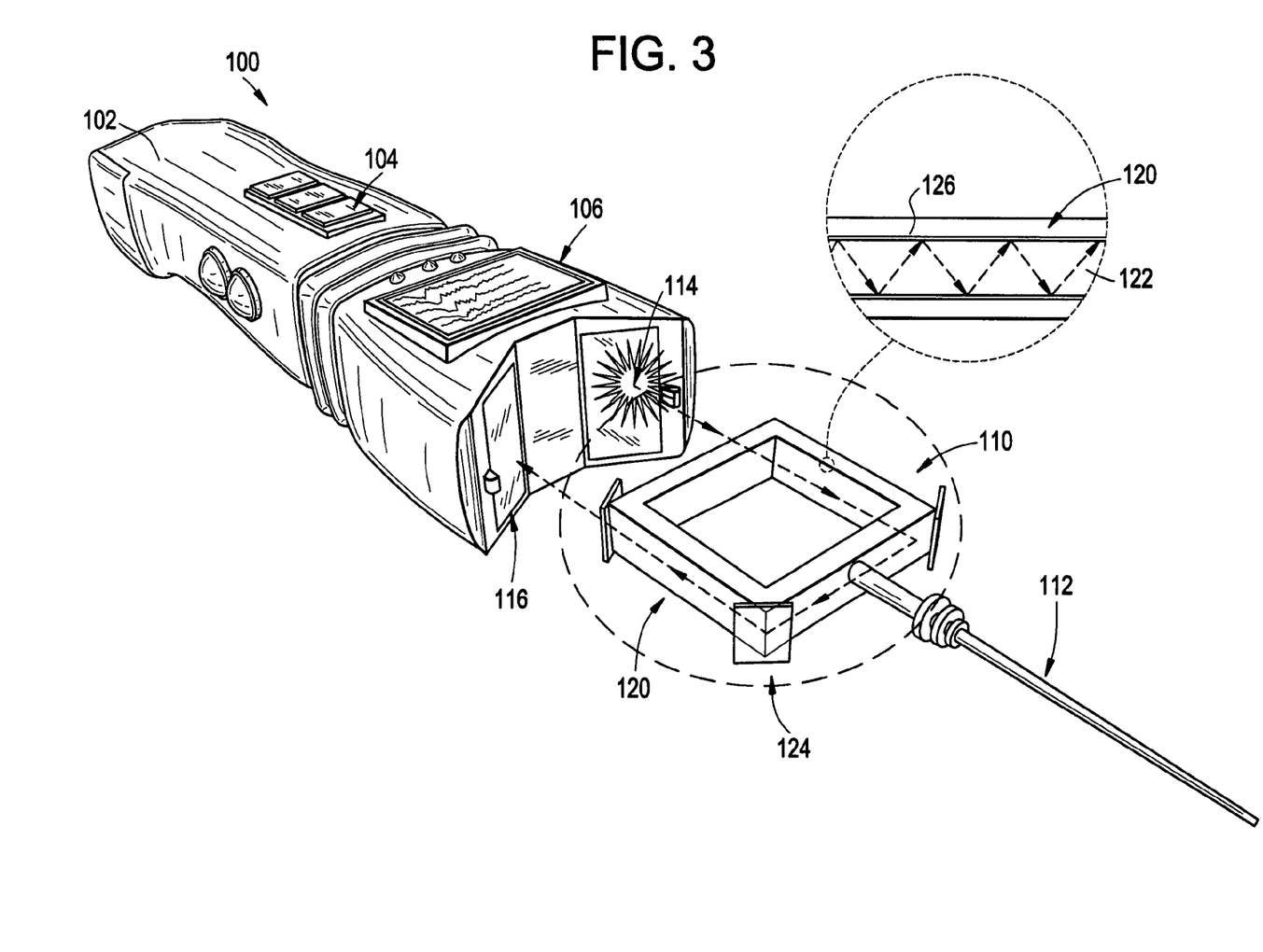

Referring initially to FIGS. 1 through 3, there are shown various perspective views of a compact, hand-held spectrometer device 100 in accordance with an embodiment of the invention. The device 100 includes a hand-held body 102 with large, user-friendly operator controls 104, a display portion 106 and optional audio alarm feature 108, and (as particularly illustrated in FIG. 1) an optional, disposable optofluidics module 110 with a fluid inlet 112 for collecting and analyzing a fluid sample. As particularly illustrated in FIG. 2, the device 100 also has an optical signal output port 114 through which an incident beam is directed, and an optical signal input port 116 through which a reflected beam is received. Registration pins 118 are provided for receiving the optofluidics module 110 thereon.

As shown more particularly in FIG. 3, the optofluidics module 110 includes a square shaped, nanoparticle channel 120 that contains a fluid sample 122 drawn therein. The channel 120 (along with semitransparent mirrors 124) also defines an optical path from the optical source output port 114 to the optical signal input port 116. When utilized, the optofluidics module 110 can enhance Raman detection in at least two aspects. First, the use of SERS (Surface Enhanced Raman) nanoparticles with capture molecules (e.g., antibodies) on sidewalls 126 of the channel 120 enhances the Raman cross-section (i.e., the detected signal). Second, the waveguide effect of the fluid containing channel 120 increases the optical path of the exciting beam, and thus the interaction between the laser and the sample generates more signal and increases the signal to noise ratio and sensitivity of the system.

Figure 4:
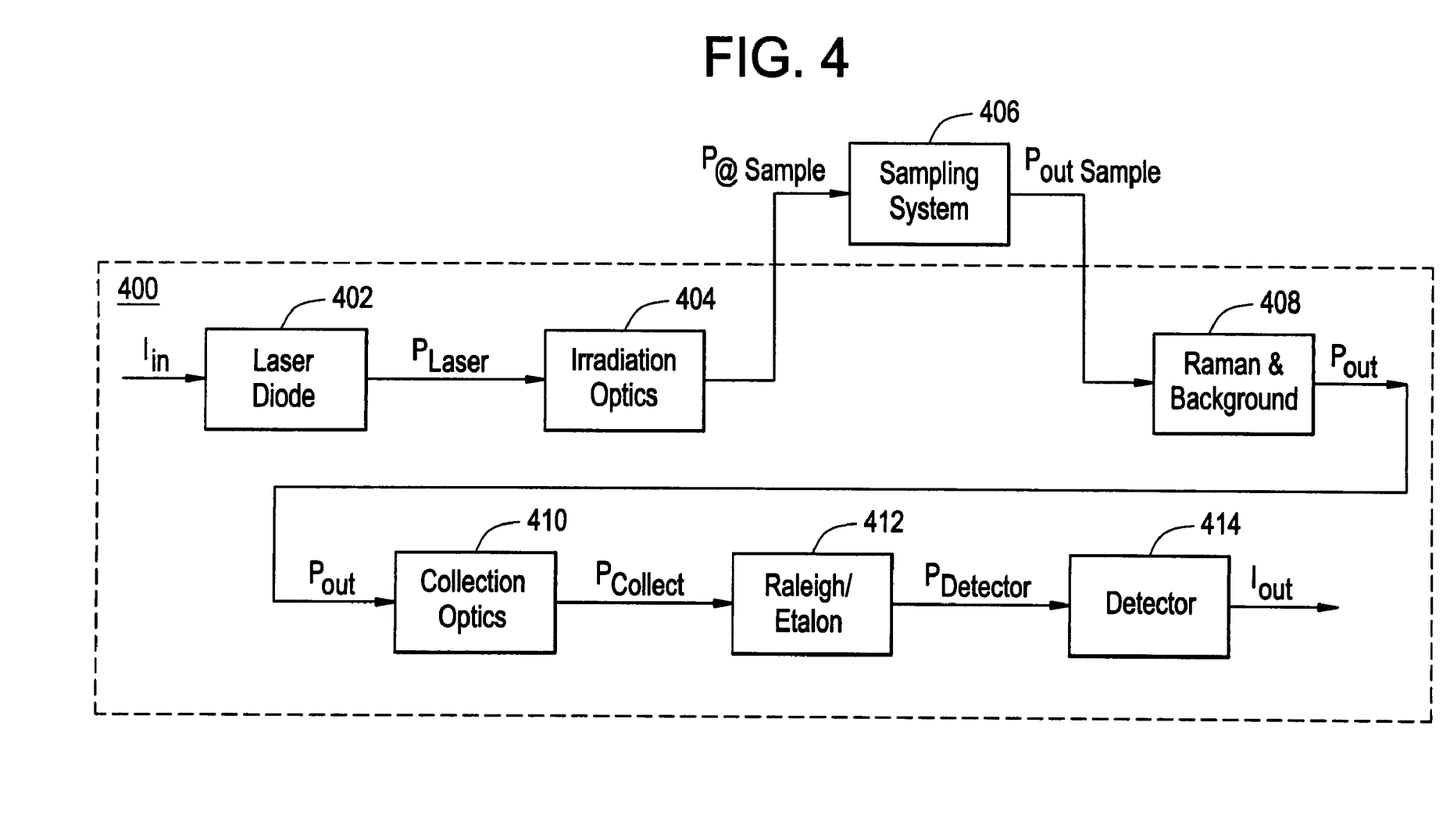
FIG. 4 is a block diagram of the interrelationship between the various integrated components of the spectrometer device of FIGS. 1-3.

Referring now to FIG. 4, there is shown a schematic block diagram of the interrelationship between various integrated components of the spectrometer system on a chip, which in turn allows for the compact scaling of a device having high resolution within a broad spectral range, low power consumption and immunity to thermal and vibration induced noises. The dashed portion of FIG. 4 represents a single chip 400, which integrates the individual components used in a Raman (for example) spectroscopy system.

More specifically, the chip 400 includes a monochromatic optical source 402, such as a laser diode, for example. The laser diode 402 may, in an exemplary embodiment, operate in the ultraviolet (UV) wavelength range. In addition, irradiation optics 404 are provided for focusing and/or collimating the output of the optical source 402 to be directed at the sample 406 to be tested. The detected optical beam scattered by the sample 406 is directed back to additional optics on the chip 400 for guiding, filtering, collimation and detection. The additional optics may include for example, Raman and background filtering optics 408, collection optics 410, and Rayleigh/etalon filtering optics 412. The filtered signal is detected by a photon detector 414, as further described herein. It will be noted that the particular sequential order in which the received optical signal is passed though various components is not necessarily limited in this manner.

Figure 5:
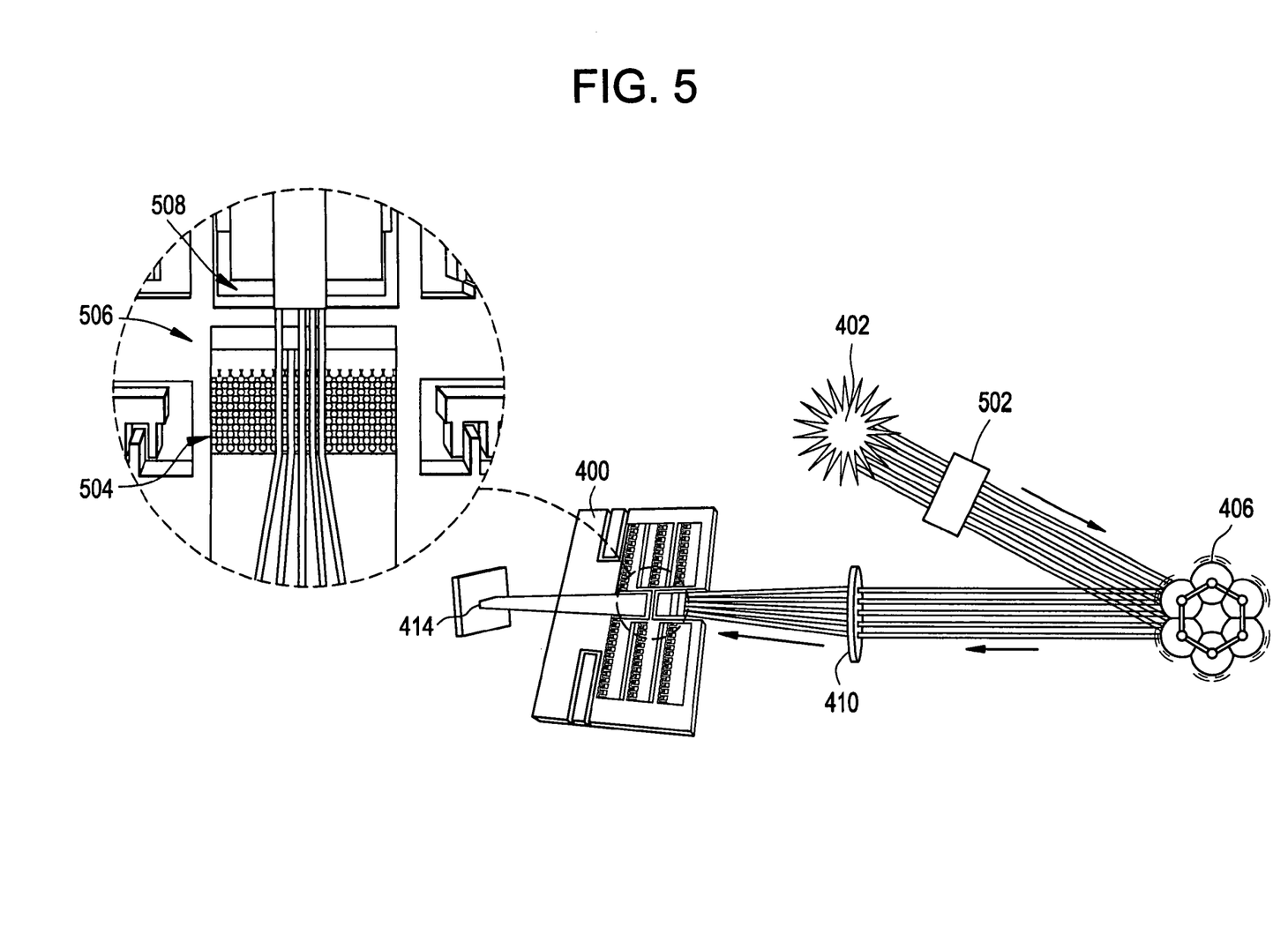
FIG. 5 is a schematic diagram illustrating the optical components of the spectrometer device of FIGS. 1-3.

FIG. 5 is a schematic diagram illustrating an exemplary arrangement of optical components of the spectrometer device on an integrated chip 400. In addition to the spectrometer system components outlined above, active control of the optical power density of the device may also be achieved through an actuator 502 (e.g., a shutter, an attenuator, a micro lens with tunable focal length) configured to selectively control the amount of optical power directed upon a particular sample 406. This may be desired, for example, in instances where the sample material is temperature sensitive for a variety of reasons. For active control, a temperature sensing device may also be integrated into the spectrometer system.

Collection optics 410 (having a high numerical aperture) receive the scattered beam from the sample 406, and may be embodied by three-dimensional photonic crystals formed on the chip substrate. Photonic crystals are periodic dielectric structures formed within a substance, and which have a band gap that prevents propagation of certain light modes. Moreover, photonic crystals are compatible with existing chip processing techniques, may serve multiple optical functions, and offer higher quality (e.g., little or no astigmatism, little or no aberrations that emanate from the fabrication techniques of conventional optics) over a broad spectral band with respect to conventional optics.

The insert portion of FIG. 5 illustrates the collimation and filtering functions in further detail. The collected beam is routed to a photonic crystal collimator 504 with a taper configured therein. Then, collimated light is passed through a photonic crystal Rayleigh filter 506 to remove the dominating Rayleigh scattered component of the scattered beam at the optical source wavelength. Because of the nano dispersive nature of the MEMS spectrograph/spectrophotometer device (Fabry-Perot filter), the component Raman wavelengths of the Rayleigh-filtered light are not spatially detected by an array of photodetectors, but are instead detected through a tunable Fabry-Perot filter 508.

As is well known, a tunable Fabry-Perot filter includes a resonant cavity and an actuator. The resonant cavity is defined by a pair of micro mirrors which can be both flat, both curved or one flat and one curved. One of the two mirrors is static while the second mirror is movable and is attached to the actuator. When broadband light is coupled to the cavity, multiple internal reflections and refractions occur and interference between transmitted beams takes place. At specific distances between the two mirrors interference is constructive and an interference pattern is produced on the other end of the Fabry-Perot. The central peak (main mode of the cavity at a specific distance between the mirrors) is a high intensity peak and the transmitted light is monochromatic.

The wavelength of the transmitted light is a function of the distance between the cavity mirrors, thus the filter is a narrow band filter. As the distance between the two mirrors is scanned continuously, multiple interferences take place leading to a continuous scan of the optical spectrum within a specific range of wavelengths. However, in contrast to conventional tunable Fabry-Perot filters, the actuation of the filter in the present disclosure is separated from the optics (i.e., the mirrors are not used as electrodes or deflectable membranes). This has the advantage of providing higher spectrograph performance, since the filter may be tuned over longer distances with lower power consumption and without introducing any deformation to the mirrors, which would adversely affect the optical quality of the filter, thus improving the bandwidth.

Figure 6:
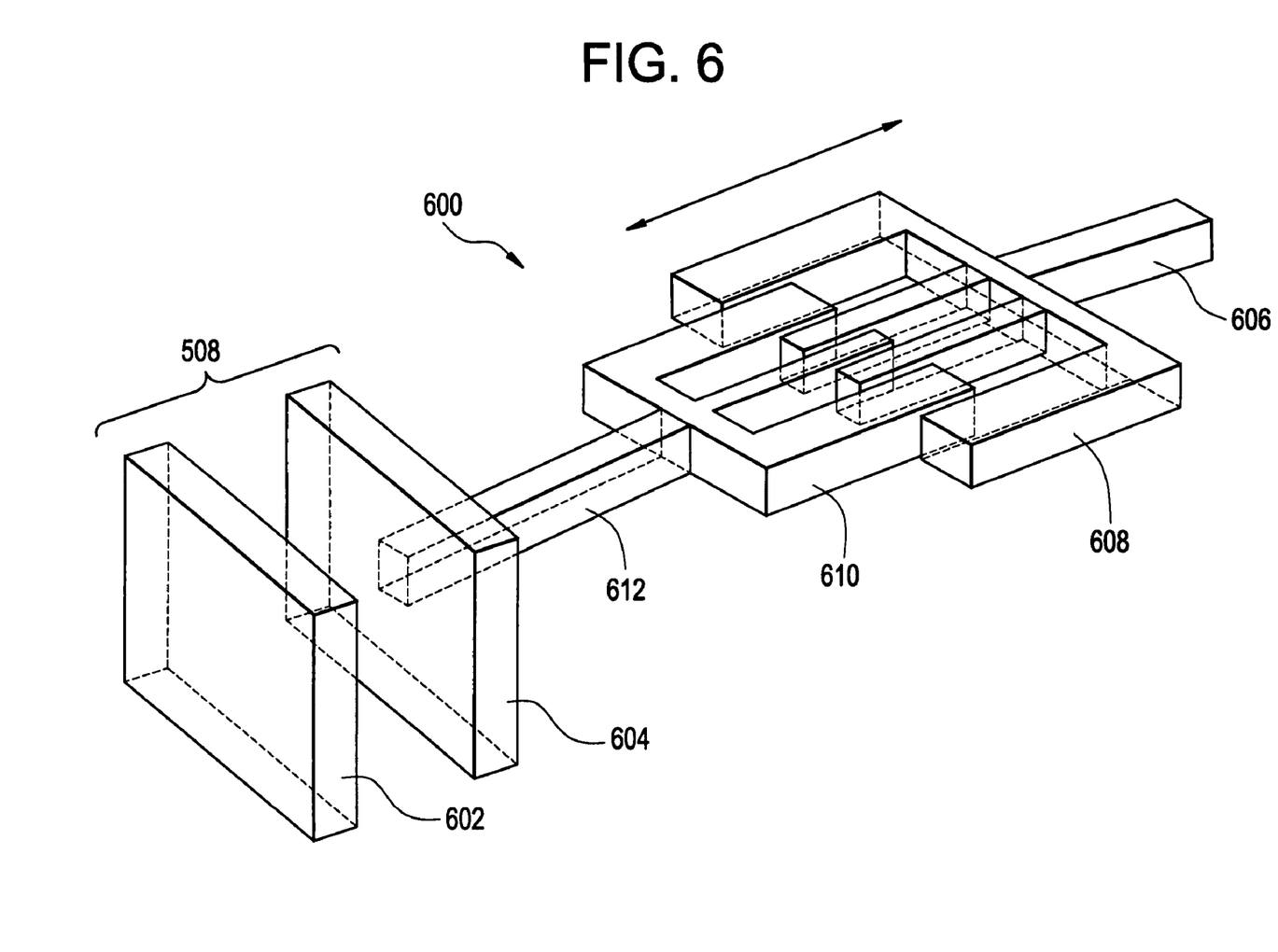
FIG. 6 is a perspective view illustrating an exemplary actuator for a tunable Fabry-Perot filter used in the spectrometer device of FIGS. 1-3, in accordance with another embodiment of the invention.

In addition, the crystallographic planes of a chip substrate (e.g., silicon) may be used to provide high smoothness, high flatness and high parallelism between the cavity mirrors, and therefore high finesse and ultimately high spectral resolution. The actuator itself may be thermal, electrostatic or magnetic in nature. In an exemplary embodiment, MEMS comb drives are used for actuation along with piano mirror cavities (i.e., both mirrors are planar). FIG. 6 is a perspective view illustrating an exemplary comb drive micro actuator 600 for a tunable Fabry-Perot filter 508, having a stationary mirror 602 and a moveable mirror 604. The actuator 600 includes a stationary portion 606 having individual comb teeth 608 intermeshed with complementary teeth 610 of a movable portion 612 coupled to the moveable mirror 604. Controlled electrostatic attraction between the teeth 608 and 610 used in the spectrometer device causes the moveable portion 612 to translate in the direction of the arrow, thus changing the distance between the mirrors 602, 604 and the cavity length as a result.

Finally, FIG. 5 also depicts a miniaturized detector 414. As opposed to conventional detection devices (e.g., charge coupled devices) that may require cooling, detector 414 may comprise a quantum dot detector array or an avalanche photodiode detector (APD), for example. The detector 414 provides a higher signal-to-noise ratio (SNR), requires little to no cooling, and may provide digital fluorescence and Rayleigh line removal.

An operation of the above described spectrometer device may be summarized as follows: A sample is excited with the photon source, the interaction between the photons and sample molecules/lattices leading to excitation of vibrational and rotational modes of molecular bonds. This inelastic interaction results in energy losses for most photons and gains for some, which then translates into wavelength shifts in the backscattered photons. This inelastic Raman scattering is again a typically very weak signal in comparison to elastic Rayleigh scattering which does not involve any energy exchange for the corresponding photons.

The low intensity of the Raman signal may be enhanced with, for example, the surface enhancing particles and waveguide feature of the optional optofluidics module. Where the optical source generates longer excitation wavelengths (NIR versus UV, for example) fluorescence can be reduced, although the tradeoff is that more power is required to excite the vibrational modes. This can otherwise result in sample burning, although an optional power management mechanism may actively reduce the optical power density incident upon the sample.

To analyze the Raman scattering (isotropic in nature), a collection probe with high numerical aperture optics is integrated into the system. The collection probe design can vary depending on the type of sample that is being analyzed (solid, liquid or gas). After signal collection, the light is filtered by means of a narrow band micromachined Rayleigh filter to reveal the Raman scattered photons. The filtered light is then focused, collimated and guided towards a MEMS tunable spectrometer (Fabry-Perot) to break it down into its spectral components.

The intensities of photons at individual wavelengths are then measured by means of a photodetector and the data is stored in memory to reconstruct the spectrum subsequently. The acquisition, and conditioning electronics are then used to produce a clean voltage output and the built in logic is used to analyze the spectrum and compare it to stored spectra to identify the chemical fingerprint of the present molecules as well as quantify their concentrations. The sample composition is then displayed on a display.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An integrated spectrometer instrument, comprising:
   an optical source formed on a chip, said optical source configured to generate an incident optical beam upon a sample to be measured;
   collection optics formed on the chip, said collection optics configured to receive a scattered optical beam from the sample, wherein said collection optics further comprise photonic crystals formed on the chip;
   filtering optics formed on the chip, said filtering optics configured to remove elastically scattered light from said scattered optical beam at a wavelength corresponding to said optical source;
   a tunable filter formed on the chip, said tunable filter configured to pass selected wavelengths of said scattered optical beam; and
   a photo detector device formed on the chip, said photo detector device configured to generate an output signal corresponding to the intensity of photons passed through said tunable filter.

2. The instrument of claim 1, wherein said collection optics further comprise a high numerical aperture lens and a collimator.

3. The instrument of claim 1, wherein said tunable filter further comprises a Fabry-Perot filter.

4. The instrument of claim 3, wherein said Fabry-Perot filter further comprises a microelectromechanical systems (MEMS) actuator coupled to a movable mirror.

5. The instrument of claim 4, wherein said MEMS actuator is configured to change the position of said movable mirror without deflection of said movable mirror.

6. The instrument of claim 5, wherein said MEMS actuator is configured to change the position of said movable mirror without application of a voltage directly thereto.

7. The instrument of claim 1, wherein said photo detector device comprises one of a quantum dot detector array or an avalanche photodiode detector.

8. The instrument of claim 1, wherein said optical source comprises an ultraviolet (UV) laser.

9. The instrument of claim 1, wherein said optical source comprises a near infrared (NIR) laser.

10. The instrument of claim 1, wherein said optical source comprises a visible laser.

11. A portable, hand-held spectrometer device, comprising:
    a body having operator controls and an output display;
    an optical signal output port through which an internally generated incident optical beam is directed, and an optical signal input port through which a sample-scattered optical beam is received;
    said incident optical beam generated by an optical source formed on a chip housed within said body;

collection optics formed on said chip, said collection optics configured to receive said sample-scattered optical beam, wherein said collection optics further comprise photonic crystals formed on the chip;

filtering optics formed on the chip, said filtering optics configured to remove elastically scattered light from said sample-scattered optical beam at a wavelength corresponding to said optical source;

a tunable filter formed on the chip, said tunable filter configured to pass selected wavelengths of said sample-scattered optical beam; and a photo detector device formed on the chip, said photo detector device configured to generate an output signal corresponding to the intensity of photons passed through said tunable filter.

12. The spectrometer device of claim 11, further comprising a detachable optofluidics module in optical communication with said optical signal output port and said optical signal input port, said optofluidics module having a fluid inlet for collecting and analyzing a fluid sample.

13. The spectrometer device of claim 12, wherein said optofluidics module further comprises a closed geometry channel configured to contain a fluid sample drawn therein.

14. A portable, hand-held spectrometer device, comprising:

a body having operator controls and an output display;

an optical signal output port through which an internally generated incident optical beam is directed, and an optical signal input port through which a sample-scattered optical beam is received;

said incident optical beam generated by an optical source formed on a chip housed within said body;

collection optics formed on said chip, said collection optics configured to receive said sample-scattered optical beam;

filtering optics formed on the chip, said filtering optics configured to remove elastically scattered light from said sample-scattered optical beam at a wavelength corresponding to said optical source;

a tunable filter formed on the chip, said tunable filter configured to pass selected wavelengths of said sample-scattered optical beam;

a photo detector device formed on the chip, said photo detector device configured to generate an output signal corresponding to the intensity of photons passed through said tunable filter; and a detachable optofluidics module in optical communication with said optical signal output port and said optical signal input port, said optofluidics module having a fluid inlet for collecting and analyzing a fluid sample, wherein said optofluidics module further comprises a closed geometry channel configured to contain a fluid sample drawn therein; and wherein sidewalls of said channel include nanoparticles formed thereon with capture molecules for surface enhanced Raman detection.

15. A portable, hand-held spectrometer device, comprising:

a body having operator controls and an output display;

an optical signal output port through which an internally generated incident optical beam is directed, and an optical signal input port through which a sample-scattered optical beam is received;

said incident optical beam generated by an optical source formed on a chip housed within said body;

collection optics formed on said chip, said collection optics configured to receive said sample-scattered optical beam;

filtering optics formed on the chip, said filtering optics configured to remove elastically scattered light from said sample-scattered optical beam at a wavelength corresponding to said optical source;

a tunable filter formed on the chip, said tunable filter configured to pass selected wavelengths of said sample-scattered optical beam;

a photo detector device formed on the chip, said photo detector device configured to generate an output signal corresponding to the intensity of photons passed through said tunable filter; and a detachable optofluidics module in optical communication with said optical signal output port and said optical signal input port, said optofluidics module having a fluid inlet for collecting and analyzing a fluid sample, wherein said optofluidics module further comprises a closed geometry channel configured to contain a fluid sample drawn therein; and wherein said closed geometry channel further comprises one of a square, rectangular, circular and hexagonal shape, configured to form an optical waveguide path between said optical signal output port and said optical signal input port.

16. The spectrometer device of claim 11, wherein said collection optics further comprise a high numerical aperture lens and a collimator.

17. The spectrometer device of claim 11, wherein said tunable filter further comprises a Fabry-Perot filter.

18. The spectrometer device of claim 17, wherein said Fabry-Perot filter further comprises a micro electromechanical systems (MEMS) actuator coupled to a movable mirror.

19. The spectrometer device of claim 18, wherein said MEMS actuator is configured to change the position of said movable mirror without deflection of said movable mirror.

20. The spectrometer device of claim 19, wherein said MEMS actuator is configured to change the position of said movable mirror without application of a voltage directly thereto.

21. The spectrometer device of claim 11, wherein said photo detector device comprises one of a quantum dot detector array or an avalanche photodiode detector.

22. The spectrometer device of claim 11, wherein said optical source comprises an ultraviolet (UV) laser.

23. The spectrometer device of claim 11, wherein said optical source comprises a near infrared (NIR) laser.

24. The spectrometer device of claim 11, wherein said optical source comprises a visible laser.

25. The spectrometer device of claim 11, further comprising an actuator for automatically controlling the amount of output optical power transmitted through said optical signal output port.

* * * * *